US006274144B1

(12) United States Patent
Wang et al.

(10) Patent No.: US 6,274,144 B1
(45) Date of Patent: Aug. 14, 2001

(54) METHOD FOR GENERATING ANTIBODIES TO SACCHARIDE FRAGMENTS

(75) Inventors: Ying Wang, Brookline, MA (US); Rawle I. Hollingsworth, Haslett, MI (US); Dennis L. Kasper, Newton Centre, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 0 days.

(21) Appl. No.: 09/488,938

(22) Filed: Jan. 21, 2000

Related U.S. Application Data

(62) Division of application No. 09/048,705, filed on Mar. 26, 1998, now Pat. No. 6,027,733.

(60) Provisional application No. 60/042,416, filed on Mar. 26, 1997.

(51) Int. Cl.$^7$ .................. A61K 39/40; A61K 39/085; A61K 39/09

(52) U.S. Cl. ..................... 424/165.1; 424/164.1; 424/178.1; 424/243.1; 424/244.1; 424/234.1; 536/123; 536/123.1; 536/124; 536/18.5; 536/514; 536/54

(58) Field of Search ................ 424/165.1, 164.1, 424/178.1, 243.1, 244.1, 234.1; 536/123, 123.1, 124, 185.5; 514/54

(56) References Cited

U.S. PATENT DOCUMENTS

| | | |
|---|---|---|
| 3,723,506 | 3/1973 | Deslongchamps ............... 260/484 R |
| 4,316,982 | 2/1982 | Holst et al. . |
| 4,356,170 | 10/1982 | Jennings et al. . |
| 5,565,204 | * 10/1996 | Kuo et al. ........................ 424/244.1 |
| 5,929,049 | * 7/1999 | Singh et al. ........................... 514/54 |
| 6,027,733 | * 2/2000 | Wang et al. ...................... 424/243.1 |

FOREIGN PATENT DOCUMENTS

| | | |
|---|---|---|
| 0371414 | 11/1989 | (EP) . |
| 0382576 | 2/1990 | (EP) . |
| 0497524 | 1/1992 | (EP) . |

OTHER PUBLICATIONS

Deslongchamps et al., "Ozonolysis of Acetals. (I) Ester Synthesis, (2) THP Ether Cleavage, (3) Selective Oxidation of β–Glycoside, (4) Oxidative Removal of Benzylidene and Ethylidene Protecting Groups", *Canadian Journal of Chemistry*, 49:2465–2467, 1971.

Deslongchamps et al., "The Importance of Conformation in the Ozonolysis of Acetals", *Canadian Journal of Chemistry*, 50:3402–3404, 1972.

Deslongchamps et al., "The Oxidation of Acetals by Ozone", *Canadian Journal of Chemistry*, 52:3651–3664, 1974.

Lee et al., "Effects of IN Vitro and In Vivo and Growth Conditions on Expression of Type 8 Capsular Polysaccharide by Staphylococcus aureus," *Infection and Immunity*, 61:1853–1858, 1993.

Paoletti et al., "Neonatal Mouse Protection against Infection with Multiple Group B Streptococcal (GBS) Serotypes by Maternal Immunization with a Tetravalent GBS Polysaccharide–Tetanus Toxoid Conjugate Vaccine," *Infection and Immunity*, 62:3236–3243, 1994.

Prieto et al., "A New Ganglioside in Human Meconium Detected by Antiserum against the Human Milk Sialyloligosaccharide, LS–Tetrasaccharide b$^1$," *Archives of Biochemistry and Biophysics*, 241:281–289, 1985.

Tzianabos et al., "Structural Characteristics of Polysaccharides That Induce Protection against Intra–abdominal Abscess Formation," *Infection and Immunity*, 62:4881–4886, 1994.

Tzianabos et l., "The Capsular Polysaccharide of Bacteroides fragilis Comprises Two Ionically Linked Polysaccharides," *The Journal of Biological Chemistry*, 267:18230–18235, 1992.

Wessels et al., "Structural Determination and Immunochemical Characterization of the Type V Group B Streptococcus Capsular Polysaccharide," *The Journal of Biological Chemistry*, 266:6714–6719, 1991.

Wiegandt et al., "Carbohydrate Components of Extraneruonal Gangliosides from Bovine and Human Spleen, and Bovine Kidney," *European Journal of Biochemistry*, 15:287–292, 1970.

Zhang, Y, et al., "Degradation of Wood Polysaccharide Model Compounds During Ozone Treatment", J. Pulp Pap. Sci. vol. 23, No. 1, 1997, pp. J23–J27, XP000973103.

Wang et al., Proc. Nat. Acad. Sci. 95(12):6584–6589, 1998.*

\* cited by examiner

Primary Examiner—Francisco Prats
(74) *Attorney, Agent, or Firm*—Fish & Richardson P.C.

(57) ABSTRACT

A method for depolymerizing polysaccharides containing into saccharide fragments using ozonolysis is described.

39 Claims, 15 Drawing Sheets

METHOD FOR GENERATING ANTIBODIES TO SACCHARIDE FRAGMENTS

CROSS REFERENCE TO RELATED APPLICATION

This application claims priority from U.S. Provisional Application No. 60/042,416 filed Mar. 26, 1997, and is a divisional of U.S. application Ser. No. 09/048,705, filed Mar. 26, 1998, now U.S. Pat. No. 6,027,733 each of which is incorporated herein in its entirety.

STATEMENT AS TO FEDERALLY SPONSORED RESEARCH

This work was supported in part by National Institutes of Health grants AI 30628, AI 75326, AI23339, and AI 25152. The government has certain rights in the invention.

BACKGROUND OF THE INVENTION

This invention is in the general field of methods of preparing saccharide fragments.

Saccharides are important as commodity chemicals and are used often in food and industrial applications. They are also important specialty chemicals in biotechnology, e.g., in the preparation of antibiotics or antibodies, as antigens for vaccines, or as diagnostic reagents.

Saccharides may be obtained from natural sources or synthesized enzymatically or chemically. Synthesis of saccharides having more than about five monosaccharide units often is difficult, especially if one of the units is sialic acid, which is acid labile. Enzymatic synthesis is limited by the available enzymes and substrates and may be relatively expensive.

While natural polysaccharides are sometimes available, in some situations, their use presents problems when they are too large. For example, many food and industrial applications require polysaccharides of specific sizes, and some native polysaccharides may be far too large. In some applications, decreasing the size of the polysaccharide can improve ease of handling and lower production costs. Where a cross-linked saccharide is desired, e.g., to enhance immunogenicity when used in a vaccine, available materials of high molecular weight may form insoluble gels when cross-linked. Reducing the chain length of the starting saccharide can avoid this problem.

Polysaccharides can be cleaved into smaller molecular weight fragments by acid, base, or enzymatic-catalyzed hydrolysis. Acid catalyzed degradation may cleave polysaccharides nonselectively in both carbohydrate and other functional moieties, yielding inconsistent products or non-functional products. For example, sialic acids are found on the carbohydrate moieties of many biologically important polysaccharides and can be determinants of biological functions, including recognition and attachment. They can also be determinants of epitopes for antibody generation and as such should be conserved in attempts to generate saccharide fragments, from polysaccharides. Sialic acids, however, are readily removed by acid.

Enzymatic hydrolysis of polysaccharides can be highly specific but it is usually limited to applications where an enzyme with the desired specificity is readily available. Some saccharide fragments may alternatively be isolated directly from natural sources, but these naturally occurring shorter polysaccharides typically exist in limited quantity. In some cases, saccharide fragments may be chemically and/or enzymatically synthesized. However, even in those cases the enzymes and substrates necessary to conduct the synthesis may be expensive. In general, the synthesis of saccharide fragments of more than five monosaccharide residues can be extremely difficult.

SUMMARY OF THE INVENTION

The invention is based on the discovery that ozone can be used to cleave polysaccharides to yield useful shorter-length saccharide fragments of a desired length, which generally retain structural features of the polysaccharide.

Accordingly, the invention features a method for producing a saccharide fragment by oxidizing a larger polysaccharide having at least one covalent bond between a C1 anomeric carbon of an aldose residue and an oxygen atom of a second monosaccharide residue in a -D glycosidic linkage. The method can also be used when the covalent bond is in the form of an -L linkage. Typically, the -D and -L linkages will exhibit similar reactivities. Similarly, the -D and -L linkages will also exhibit similar reactivities. The method comprises protecting free hydroxyl groups on the larger polysaccharide; reacting the larger polysaccharide with ozone to oxidize the C1 anomeric carbon, thus converting the aldose residue into an aldonic acid ester residue; and cleaving the aldonic acid ester residue to form the saccharide fragment.

In another aspect, the invention features a method of preparing an saccharide fragment by oxidizing a larger polysaccharide having at least one covalent bond between a C1 anomeric carbon of an aldose residue and an oxygen atom of a second monosaccharide residue in an or glycosidic linkage (henceforth, referred to as the "one-step" method).

The glycosidic linkage can be in any form, e.g., -L, -D, -L or -D. As is mentioned above, the -D and -L linkages will typically exhibit similar reactivities, and the -D and -L linkages will exhibit similar reactivities.

The one-step method comprises reacting the larger polysaccharide with ozone to cleave a bond linking two monosaccharide subunits in the polysaccharide, resulting in the formation of the saccharide fragment.

The larger polysaccharide in the methods described herein can be from any source and can contain labile residues, e.g., sialic acid. Preferably, the larger polysaccharide is substantially pure. The larger polysaccharide is substantially purified when it is separated from those cellular components which accompany it in its natural state. Similarly, the saccharide fragment may optionally be subsequently purified. By a purified saccharide fragment is meant a saccharide fragment separated from the starting polysaccharide.

For purposes of diagnosis and vaccine development, the polysaccharide may be from a bacterial pathogen, e.g., a group B Streptococcus capsular polysaccharide, such as GBS type I, II, III, IV, V, VI, VII, and VIII; the O-antigen of a lipopolysaccharide; a capsular polysaccharide of *Staphylococcus aureus*, e.g., the *Staphylococcus aureus* type 5 or type 8 antigens; the capsular polysaccharide of *Streptococcus pneumonia*; and the capsular polysaccharide of *Bacteroides fragilis*.

The ozone can be added in solution, generated in-situ, or be delivered from an external source, e.g., bubbled in.

The aldonic acid ester intermediate can be cleaved by a nucleophile, e.g., a hydroxyl ion, an amine, a thiol, or a carbanion. The aldonic acid ester intermediate may alternatively be cleaved by heating or hydrolysis.

The invention also includes a method for producing antibodies using saccharide fragments produced by ozonolysis. The saccharide fragments can be conjugated to a carrier to create an immunogen, after which the immunogen is injected into a suitable host. Any recognized host is suitable, e.g., rabbit, rat, mouse, goat. Either polyclonal or monoclonal antibodies can be generated.

The invention has many advantages. The methods enable degradation of any polysaccharide containing a glycosidic linkage. The one-step procedure allows ozonolysis to take place in an aqueous solution and without the need for pretreating the starting polysaccharide. In addition, the one-step procedure can be used to depolymerize polysaccharides containing any glycosidic linkage.

If cleavage takes place at the same glycosyl residue, saccharide fragments with the same repeating unit structure can be recovered from abundant, naturally occurring polysaccharides.

Saccharide fragments produced by this method can be easily modified and linked to other molecules (e.g., protein carriers). This can make them useful in drug and vaccine design. The saccharide fragments may also be tagged with chromophores, biotins, peptides, and lipids and thus have diverse potential applications.

A still further advantage of the invention is that it is possible to vary the molecular weight of saccharide fragments generated by varying the ozonolysis conditions. As used herein, "saccharide fragment" is any complex carbohydrate which is formed according to the invention from a starting material which is a "starting polysaccharide". Thus, while the product is always smaller than the starting material, no particular size limitation is implied on either the starting material or the product. The size of the starting material generally will be dictated by the source of polysaccharide that is readily available. The size of the saccharide fragment will be a function of various factors, such as the desire for a small molecule that is more conveniently adapted to the end use (e.g., solubilized or reacted with labels), consistent with the need to conserve configuration or properties (e.g., immunological properties) of the larger starting material. In general the polysaccharide starting material will have more than 10 saccharide units, and it will be of a size dictated by its natural source and techniques for recovering it from that source. The resulting saccharide fragment cleavage product will have more than 1 unit, and typically will be smaller than 100 units. The saccharide fragments produced by the invention may in some cases be much longer than 100 units. When the term "oligosaccharide" appears herein, it is understood that the term is synonymous with "saccharide fragment".

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

DETAILED DESCRIPTION OF THE INVENTION

Figure 1A:
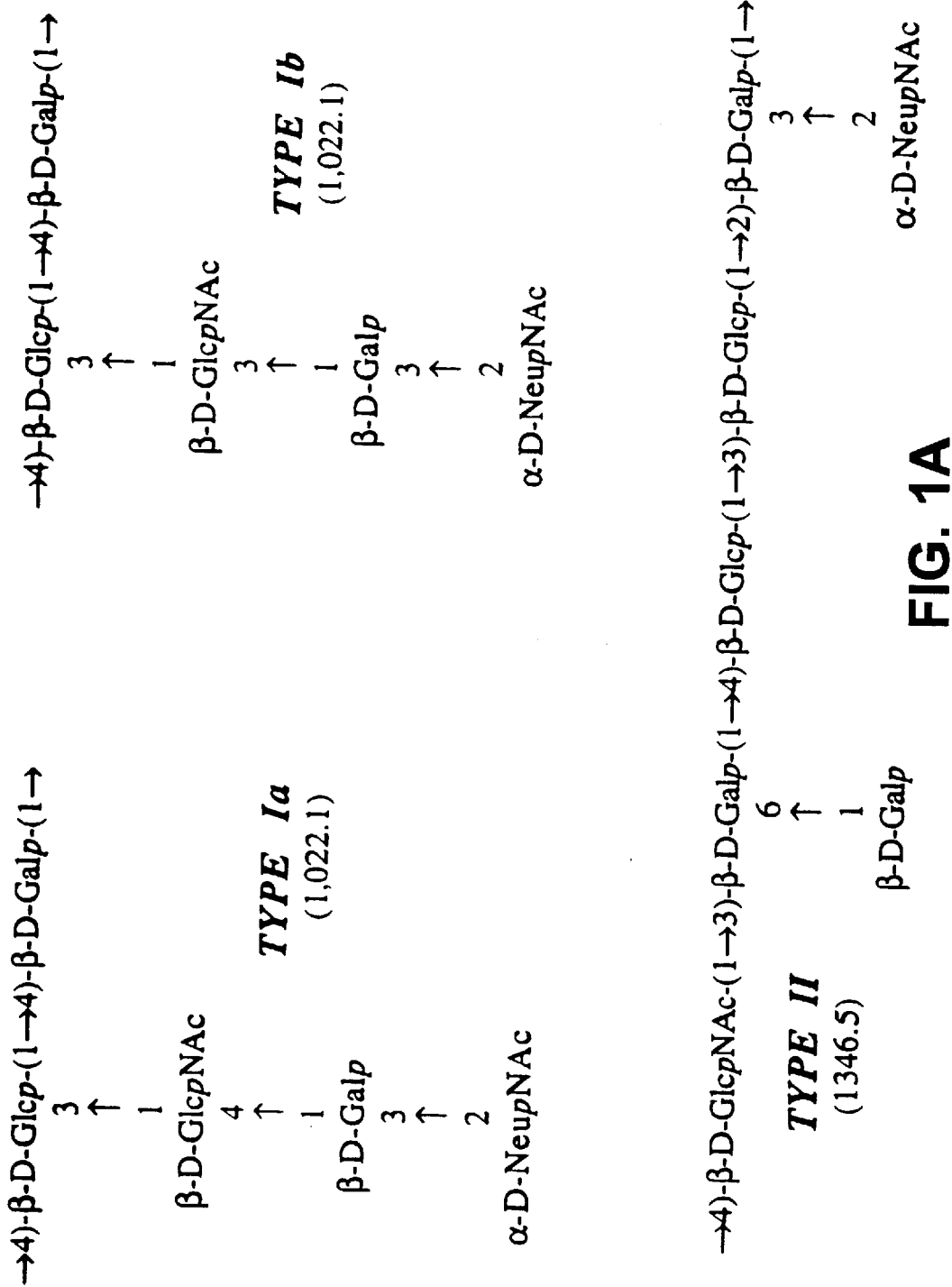
FIGS. 1A–1D are a diagram showing the repeating unit structure of GBS (Group B streptococcal) capsular polysaccharides.
Figure 1B:
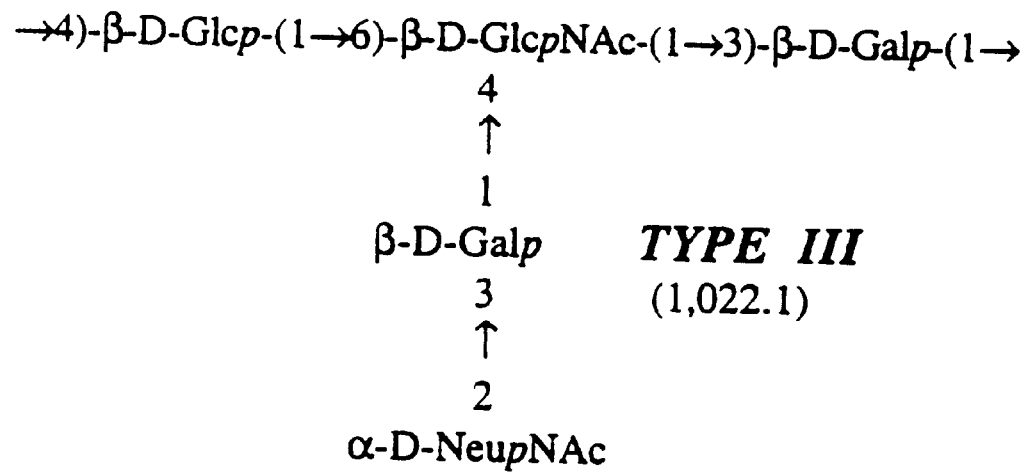
Figure 1B:
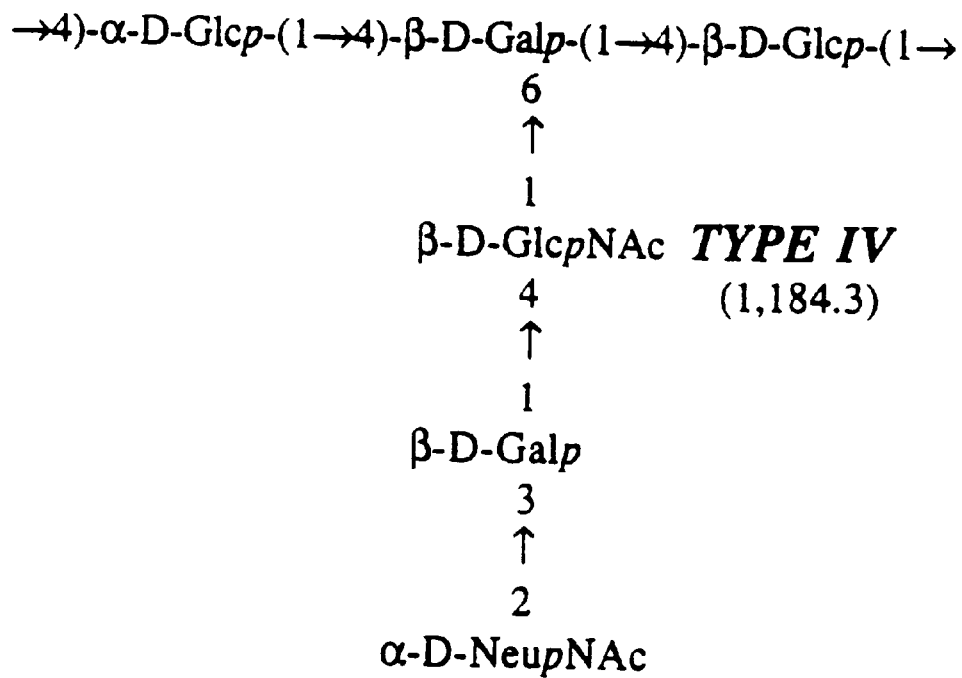
Figure 1C:
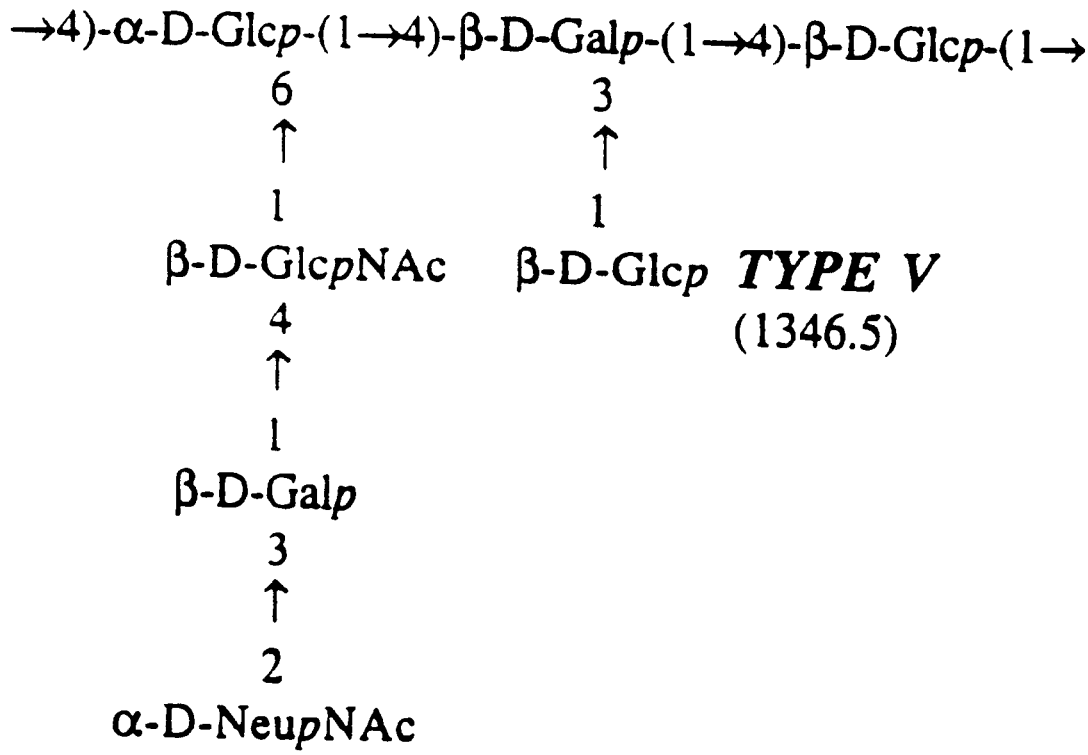
Figure 1C:
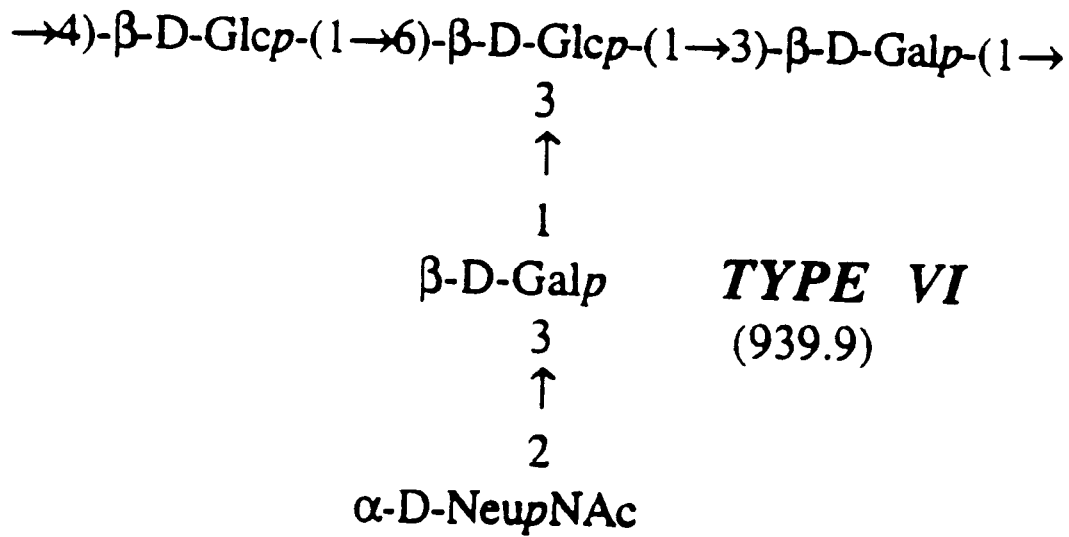
Figure 1D:
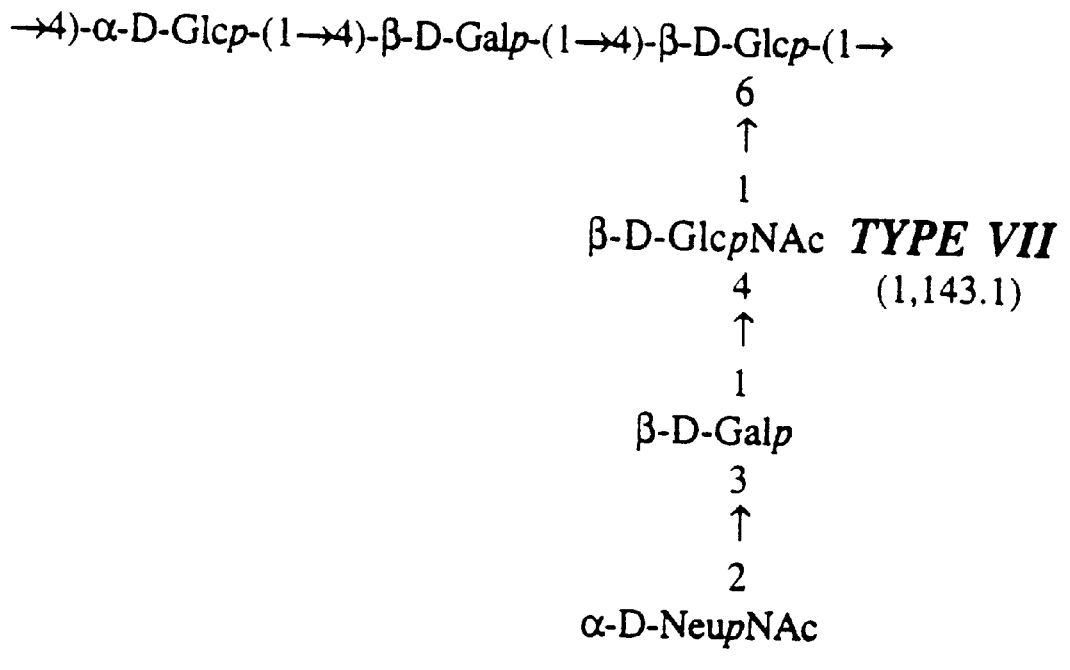
Figure 1D:
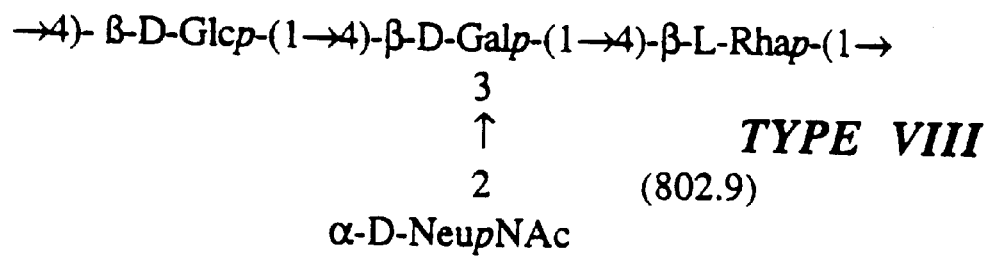

The invention provides new methods for cleaving polysaccharides using ozonolysis. In one method, ozonolysis is carried out in three steps: 1) hydroxyl groups on the polysaccharide are protected; 2) ozone is applied to the protected polysaccharide to form a partially oxidized intermediate containing an aldonic acid ester; and 3) the aldonic acid ester intermediate is deprotected and hydrolyzed, thereby cleaving the starting polysaccharide into saccharide fragments.

In a second method, ozonolysis is carried out in one step: ozone is applied directly to a polysaccharide, which can contain saccharide subunits joined in either or linkages, in an aqueous solution. When the polysaccharides are joined in a -D glycosidic linkage, ozonolysis may generate an ester or a lactone as described above.

Any polysaccharide is generally a suitable starting material for the ozonolysis methods. Polysaccharides can be purchased commercially or isolated from natural sources by standard methods. For example, polysaccharides can be isolated from bacterial species by methods described by Wessels et al., J. Biol. Chem. 266:6714 (1991), Tzianabos et al., J. Biol. Chem. 267:18230 (1992), and Lee et al., Infect. Immun. 61: 1853 (1993).

Ozonolysis Using the Three-Step Method

This method can be used to selectively depolymerize polysaccharides containing a -D or -L glycosidic linkage. The first step of the method protects the free hydroxyl groups of the polysaccharide from subsequent treatment with ozone. Among the available protection methods, peracetylation is generally preferred, although other methods such as persilylation and permethylation are also suitable. Peracetylation is usually accomplished by treating polysaccharides with acetic anhydride and pyridine; however, acetic anhydride/ potassium acetate or acetate anhydride/sodium acetate and the like can also be used as acetylation reagents.

If the polysaccharide is not soluble in acetic anhydride/ pyridine, a cosolvent such as formamide may be added. The reaction time can be shortened by increasing the temperature. For example, the reaction takes place either overnight (in 12–24 hours) at room temperature, or in 2 hours at 70° C.

Upon completion of the peracetylation reaction, the excess reagents and solvents are removed using procedures known in the art. For example, the reaction mixture can be dialyzed against distilled water, after which the water is removed by lyophilization or evaporated under nitrogen or on a rotary evaporator. Alternatively, the solvent can be directly removed using a rotary evaporator. Direct removal typically requires heating or the addition of ethanol to speed the evaporation of pyridine and formamide.

In the next step, the protected polysaccharide is dissolved in ethyl acetate, acetic anhydride/potassium acetate, or another ozone-inert solvent such as dichloromethane or tetrahydrofuran. The solution is sonicated for a few minutes to dissolve the polysaccharide, after which ozone is added at room temperature. To reduce the amount of solvent evaporated, a condensation device can be used during the ozone application step.

The application of ozone to the protected polysaccharide results in the formation of an aldonic acid ester intermediate. Various methods of applying the ozone may be used. For example, ozone can be delivered from an external ozone generator (More-Zon10, More Production, Taiwan), which creates ozone electronically from oxygen or air. Other ozone application methods may also be used. After ozone treatment, the solvent is evaporated on a rotary evaporator.

In the third step, the aldonic ester linkages in the polysaccharide can be hydrolyzed with a base such as 0.1 N NaOH at room temperature for 30 minutes, which simultaneously removes the protecting group. The nascent oligomers can alternatively be liberated, and the termini simultaneously functionalized, with another nucleophile known to cleave ester bonds. Appropriate nucleophiles include (but are not limited to) alkoxides, phenoxides, carbanions, thiols, and hydrazines. The use of an, -diamine, for example, leads to an amide linkage of the saccharides to one end of the amine, with the free amino group available for coupling to a carrier or support matrix.

Alternatively, the aldonic esters may be converted to lactones by simple heating, and the acetyl protecting groups may then be removed in a separate subsequent step.

Ozonolysis Using the One-Step Method

In the one-step method, degradation of the polysaccharide is accomplished in one step by treating the polysaccharide solution with ozone. The polysaccharide substrates are dissolved in any suitable aqueous solvent or buffer solution, e.g., water. For degrading polysaccharides containing acid-sensitive residues, the reaction is preferably carried out in a basic buffer (e.g., phosphate buffered saline, or sodium bicarbonate) to prevent the loss of acid-sensitive groups. Acid formed during the ozonolysis reaction may also be neutralized with a base such as alkali, alkali carbonates, bicarbonates, hydroxides, or other inorganic or organic bases.

Polysaccharides containing either or linkages, including -L, -D, -L or -D linkages, are suitable starting products for the one-step ozonolysis method. When the polysaccharide contains a -D or -L linkage, it forms a partially oxidized intermediate containing an aldonic acid ester, which forms a lactone and automatically cleaves the polysaccharide. Ozone treatment will preferentially affect the -D or -L linkages; thus, in relatively brief exposures to ozone, polysaccharides containing -D or -L linkages can be preferentially depolymerized at these sites.

When polysaccharides are exposed to ozone for lengthy periods of time in an aqueous solution, additional reactions can occur that can result, e.g., the formation of radicals, in cleavage of glycosidic bonds in the polysaccharide, oxidation of the polysaccharides, or the formation of acids. Because these reactions do not require the presence of a -D or -L glycosidic linkage, they can be used to cleave polysaccharides containing only linkages (e.g., dextran or starch). By monitoring the extent of ozonolysis, e.g., by monitoring products subjected to ozonolysis for varying lengths of time, the desired reaction products can be obtained.

Further Processing of Saccharide Fragments Generated Using Ozonolysis

The products resulting from the ozonolysis methods are saccharide fragments terminating with a carboxylate group. The carboxylate group can be activated with carbodiimides that function as zero-length cross-linking agents and couple the saccharides to amine-containing molecules.

All the resulting saccharide fragments may be further manipulated for other purposes. Saccharide fragments that contain one or more diol function groups may be selectively oxidized with sodium metaperiodate to create aldehyde groups. For example, sialic acid can easily be oxidized by sodium periodate to create a free aldehyde group at the C8 position. Such saccharide fragments may then be coupled to molecules containing amine moieties, such as proteins, or to a bifunctional molecule that serves as a spacer and can be further coupled to another molecule.

For polysaccharides containing -D linkages, the ozonolysis-mediated cleavage is highly selective in that ozone reacts selectively at these linkages; however, the cleavage site is generally random among all the same -D glycosidic linkages within a polysaccharide. The size distribution of saccharides may be controlled by controlling ozonolysis conditions, including the concentration of the polysaccharide, the reaction time, the rate of ozone passing through the reaction mixture, and the total amount of ozone consumed. For example, longer reaction times and consumption of more ozone result in smaller saccharides. Controlled cleavage of the polysaccharide thus results in a mixture of saccharides with a desired, narrow range of sizes which retain the repeating-unit structures of the parent polysaccharide.

The products of the ozonolysis reaction can be separated by techniques well known in the art, e.g., gel-filtration, size-exclusion, or ion-exchange column chromatography. The eluent can be a suitable buffer, such as PBS, TRIS, or distilled water. Fractions are monitored by a refractive index detector or are assayed for carbohydrate contents. Fractions representing different-sized saccharides are pooled and analyzed by spectroscopic methods, typically NMR spectroscopy. The sizes of the resulting saccharide fragments are determined either by mass spectrometry (e.g., electrospray) or by measurement of their elution volume and calculation from the calibration curve of the column. Maintenance of polysaccharide function can be verified by an appropriate assay (e.g., an ELISA).

An important class of polysaccharides suitable for use in the invention include bacterial capsular polysaccharides and lipopolysaccharides, e.g., those from the pathogenic bacteria group B Streptococcus, *B. fragilis, S. aureus*, and *S. pneumoniae*. Protective polysaccharides associated with these bacteria contain labile sialic acid or pyruvyl (carboxyethylidene) residues that are critical to protective epitopes.

The saccharide fragments generated from these polysaccharides by ozonolysis can be used as diagnostic reagents, therapeutic reagents, or as reagents for the preparation of vaccines. In these applications, fragments of the outer polysaccharide coats of the organisms can be incorporated into a molecular matrix or attached to a carrier.

The following non-limiting examples are used to describe the generation of saccharide fragments by ozonolysis and uses of the saccharide fragments so generated.

EXAMPLES

Materials and Methods

Unless otherwise indicated, the following materials and methods were used in performing the experiments described in the following examples.

Group B Streptococcus capsular polysaccharides were isolated and purified as described by Wessels et al., J. Biol. Chem. 266:6714 (1991). Preparation of polysaccharide A of *Bacteroides fragilis* was as described by Tzianabos et al., J. Biol. Chem. 267:18230 (1992), and the preparation of the capsular polysaccharide of *Staphylococcus aureus* type 5 was as described by Lee et al., Infect. Immun. 61: 1853 (1993). Desialyated GBS has a structure identical to the polysaccharide of *Streptococcus penumoniae* type 14. It was obtained by mild acid hydrolysis to remove the sialic acid from the GBS polysaccharide as follows: One 10 mg sample of GBS type III polysaccharide was added to 5 ml of 6% acetic acid and heated at 80 C. for 1 hour. The sample was then dialyzed against deionized water and freeze-dried. Dextran was purchased from Pharmacia (Piscataway, N.J.).

Superdex75 and Superose12 columns were obtained from Pharmacia LKB Biotechnology, Inc.

Peracetylation

A 10 mg sample of polysaccharide was dissolved in 5 ml of formamide and treated with 1 ml of pyridine and 0.5 ml of acetic anhydride. The mixture was magnetically stirred at room temperature for 16 hrs, then dialyzed extensively against distilled water and freeze dried.

Ozone Treatment

A 10-ml volume of ethyl acetate was added to the dried product, and the mixture was bubbled with 21% ozone at a flow rate of 3.17 ml/sec for 5 hours unless indicated otherwise. Ozone was generated from compressed air or oxygen through an ozone generator (More-Zon10). The solvent was then removed by evaporation on a rotary evaporator.

For the one-step ozonolysis procedure, ozonolysis was carried out in an aqueous buffer. A 10 mg sample of polysaccharide was dissolved in 2 ml of water and bubbled for the indicated period of times. Polysaccharides containing acid-sensitive groups such as those from GBS and *B. fragilis* were dissolved in either 0.2 M PBS ph 7.2 or 0.1 M NaHCO$_3$ pH 8.6.

Hydrolysis of the Ester Intermediate

In alkaline hydrolysis, the dried, oxidized material was mixed with 5 ml of 0.1N NaOH at room temperature for 2 hours and then neutralized with dilute acetic acid or hydrochloric acid. For allylamine hydrolysis, the oxidized product was treated with 5 ml of allylamine at room temperature for 30 min. The excess allylamine was evaporated under a stream of nitrogen in a hood.

Separation of Saccharide Fragments

The saccharide mixture was separated with an FPLC system (Pharmacia) using a Superdex 75 or Superdex 30 column by eluting with 0.3 mM PBS buffer with 0.025% azide at pH 7.2. Fractions were monitored by a refractive index detector. Those in desired size ranges were pooled and analyzed by spectroscopic methods. The columns were calibrated with dextran standards, and the molecular weights of saccharide fragments were obtained from column calibration curves.

In experiments using the one-step ozonolysis method, the sizes of saccharides were obtained using a Superose 12 column that had been calibrated with a dextran standard. The sizes of the saccharides were calculated from their molecular size versus their elution volume function. The structures of the polysaccharides were analyzed by $^1$H NMR spectroscopy.

Instrumental Methods

NMR analyses were performed on a Varian VXR500 spectrometer (Palo Alto, Calif.) or a Bruker AMX 500 with a proton resonance frequency of 500 MHz. $^1$H spectra were recorded at 70° C. in D$_2$O. Proton chemical shifts were referenced relative to water resonance calibrated at 4.290 ppm at 70° C., 4.632 ppm at 37° C., and 4.755 ppm at 25° C.

Example 1

Generation of Saccharide Fragments from Type II GBS Polysaccharides Using the Three-step Ozonolysis Procedure Type II GBS polysaccharide (FIG. 1A) was prepared as described and treated with ozone for five hours. The saccharide fragments were separated on a Superdex 75 column (HiLoad™16/60, prep grade, Pharmacia), which has a size separation range of 0.5–30 kDa. The fractions were monitored by a differential refractometer (WATERSR401, Millipore Corp., Bedford, Mass.).

Figure 2:
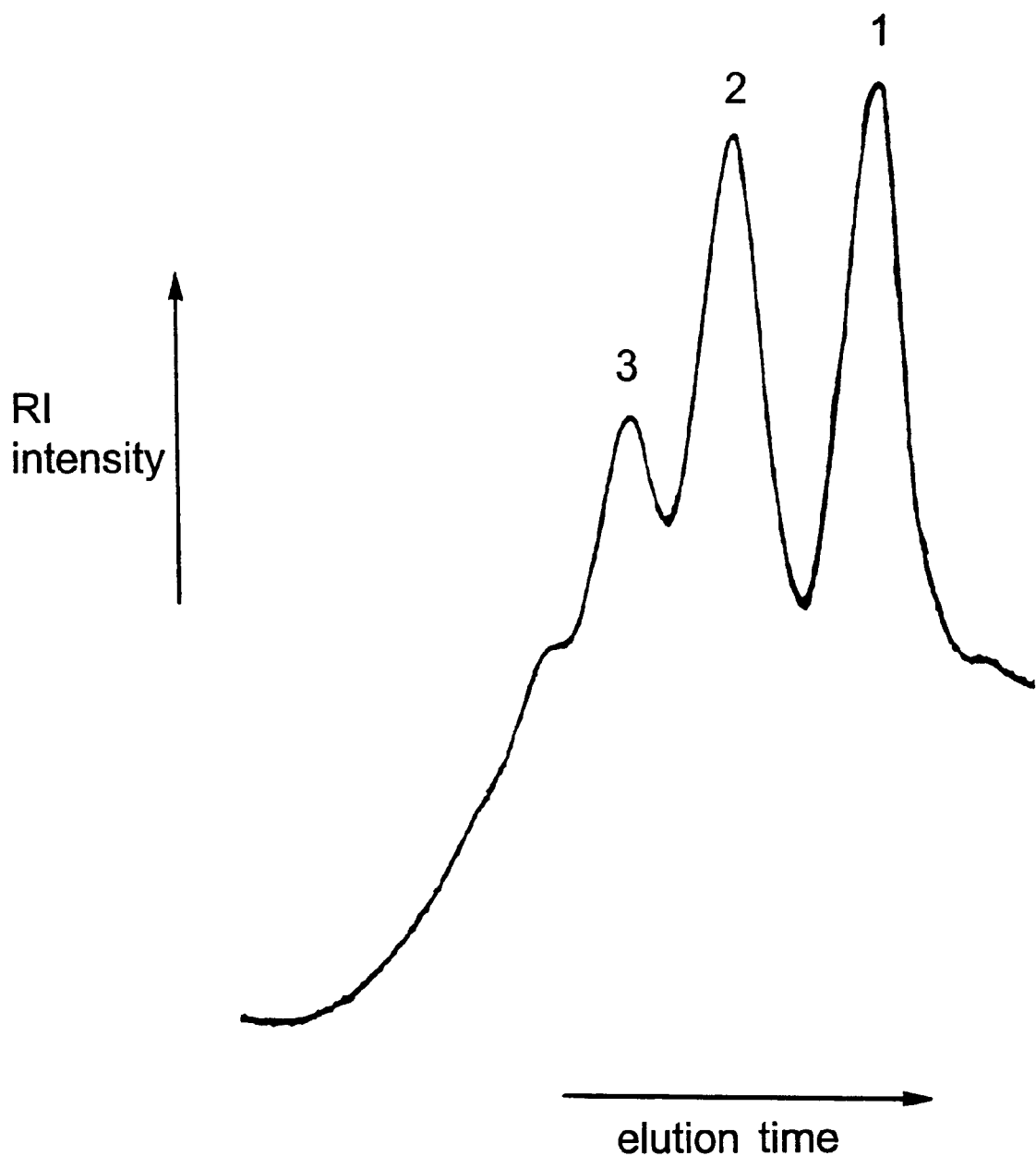
FIG. 2 is a graph showing the elution profile following liquid chromatography of saccharide fragments generated from type II GBS polysaccharide after treatment with ozone.

The eluted fractions are shown in FIG. 2. Three peaks were detected and designated 1, 2, and 3. Based on the column calibration curve, peaks 1 and 2 had average molecular weights of 2.7 kDa and 4.3 kDa, respectively. As the native type II GBS polysaccharide has a heptasaccharide repeating unit of 1.3 kDa, these peaks corresponded to two and three repeating units, respectively. At peak 3 and the higher molecular weight peaks, saccharide fragments with four and more repeating units elute.

Figure 3A:
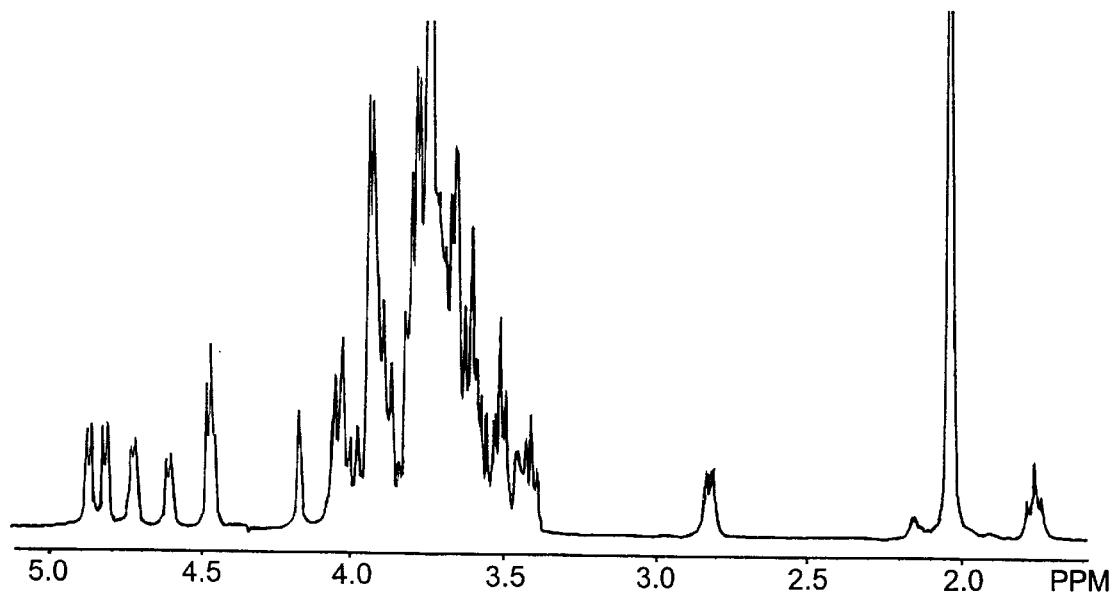
FIGS. 3A–D are the $^1$H NMR spectra of type II GBS native polysaccharide and the saccharides of peaks 3 to 1 of FIG. 2, respectively.

The $^1$H NMR spectra of the type II GBS native polysaccharide and the saccharide fragments of peaks 1–3 are shown in FIGS. 3A–D. The NMR structure of the native polysaccharide reveals a heptasaccharide repeating unit, as indicated by the six anomeric protons between 4.4 ppm and 5.2 ppm from the hexose residues, along with a sialic acid residue, as revealed by its $^1$H-resonance at 2.85 ppm and 1.86 ppm (FIG. 3A).

Figure 3B:
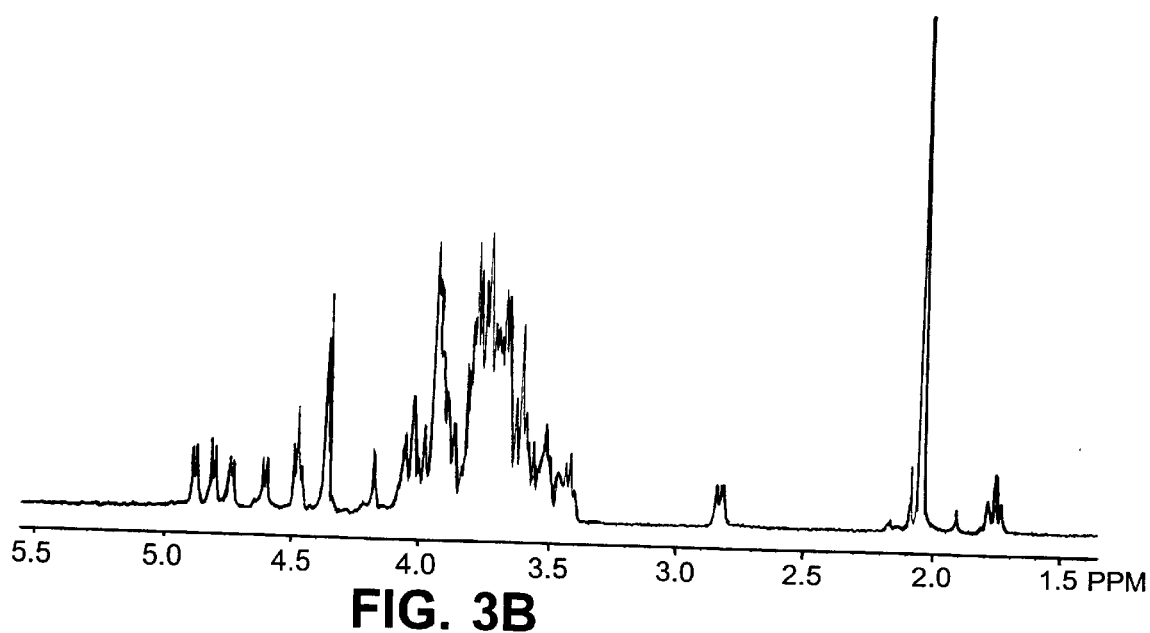
Figure 3C:
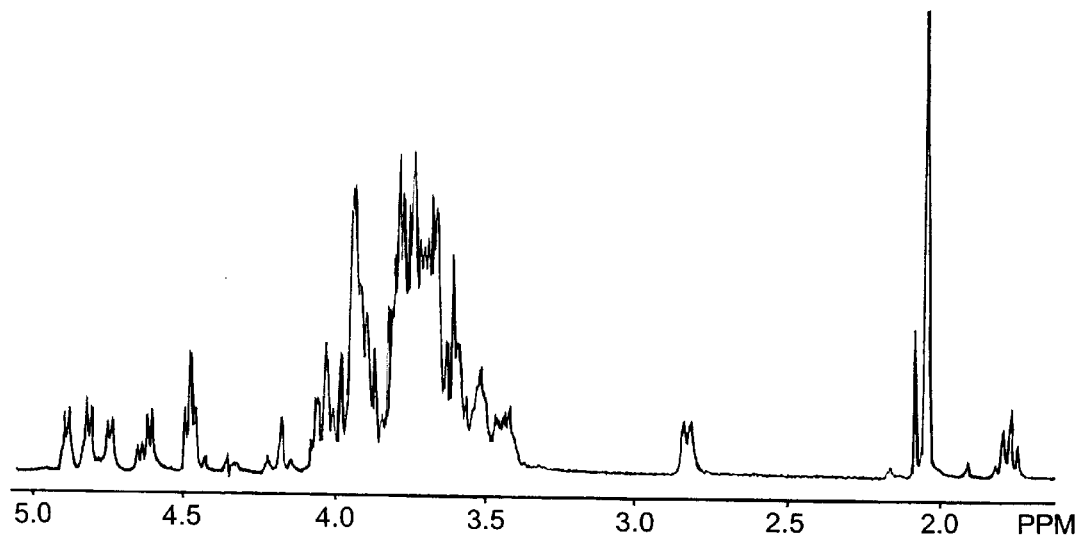
Figure 3D:
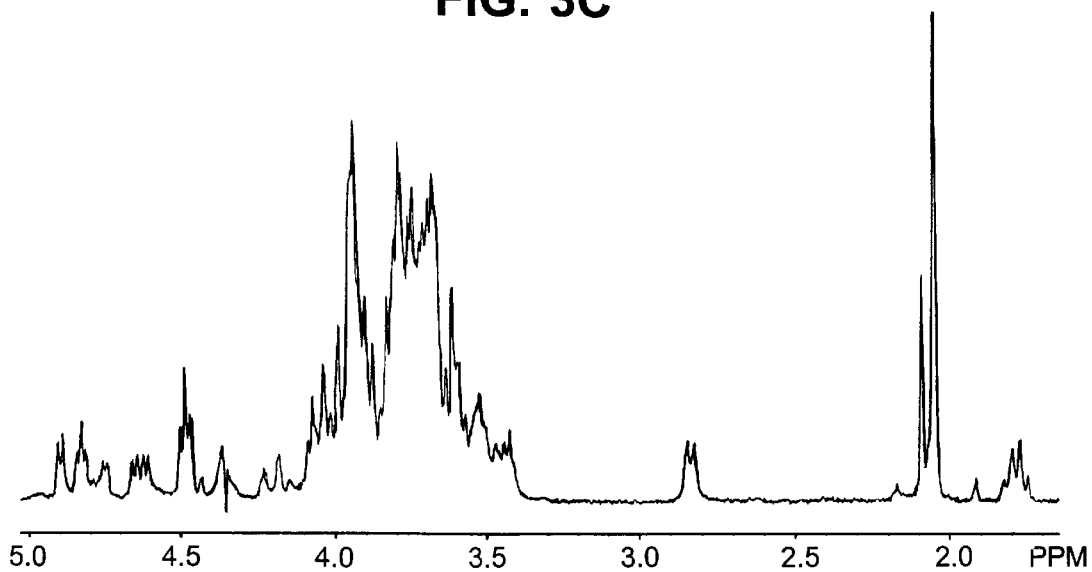

FIG. 3B shows that the majority of peak 3 is a saccharide fragment of four repeating units with an NMR spectrum identical to that of the native polysaccharide. Similarly, FIGS. 3C and 3D demonstrate that peaks 2 and 1 correspond to saccharides of three and two repeating units, respectively. In FIG. 3D, the 11 anomeric signals at 4.90 ppm (2), 4.84 ppm (2), 4.76 ppm, 4.66 ppm, 4.62 ppm, and 4.50 ppm (4) correspond to the 11 hexose residues, along with two sialic acid residues and a terminal aldonic residue, of the two repeating units. The sialic acid residue is retained in all fragments, as indicated by its $^1$H signals at 2.85 ppm and 1.86 ppm in all the spectra.

Example 2

Figure 4:
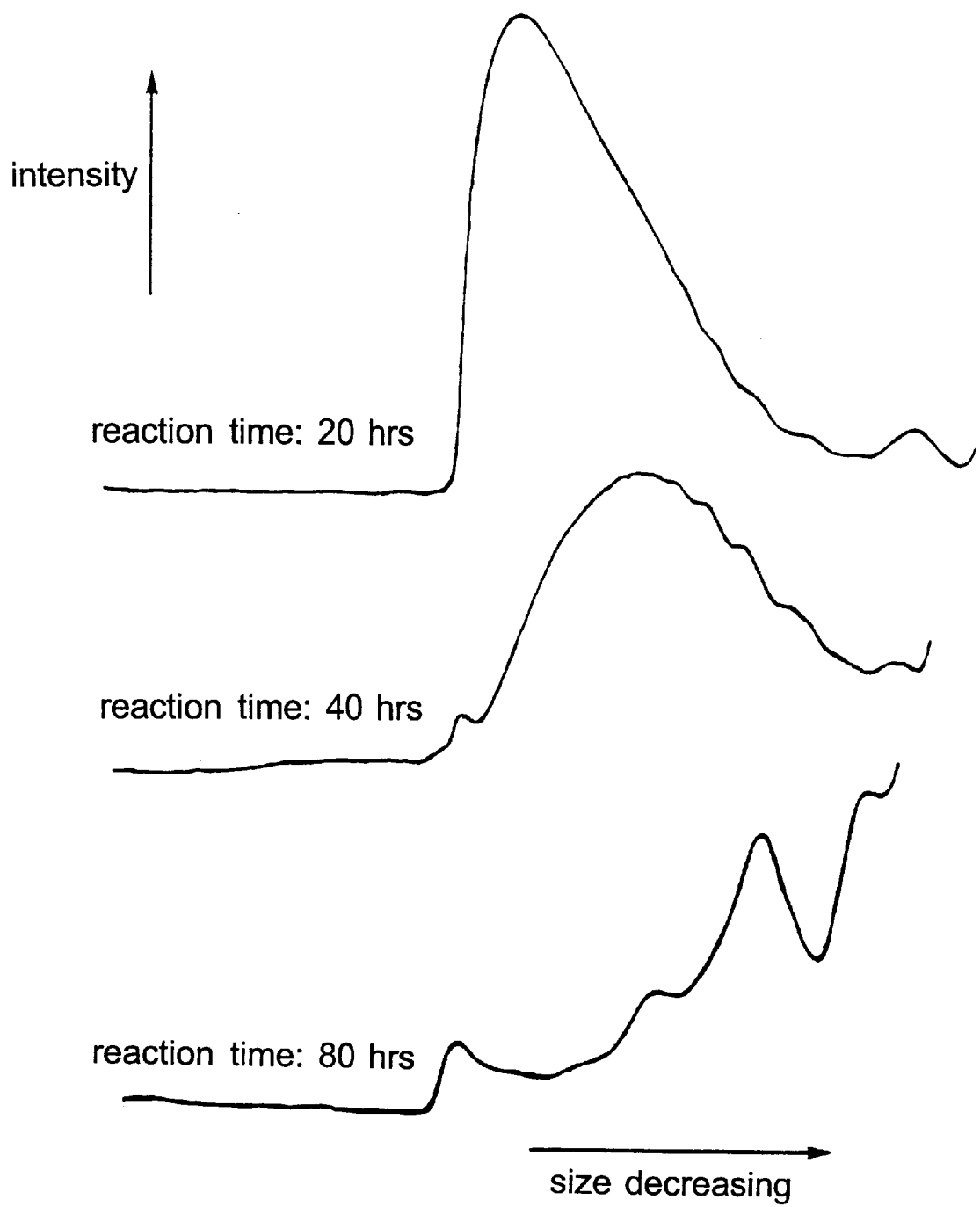
FIG. 4 is a graph showing the elution profile of saccharide fragments generated from type VIII GBS polysaccharide after treatment with ozone for the indicated amounts of time.

Generation of Saccharide Fragments from Type VIII GBS Polysaccharides Using the Three-step Ozonolysis Procedure Following Ozonolysis for Varying Amounts of Time The LC profile of type VIII GBS polysaccharide exposed to ozone for 20, 40, or 80 hours is shown in FIG. 4. The saccharide fragments were separated on a Superdex 75 column (separation range, 0.5–30 kDa), with 0.3 mM PBS as the elution buffer. As the reaction time increased, the average size of the saccharide fragment decreased. After 40 hours, the average size of the saccharides was 15 kDa. After 80 hours, the major product corresponded to a tetrasaccharide repeating unit with a molecular weight of 803.

Figure 5:
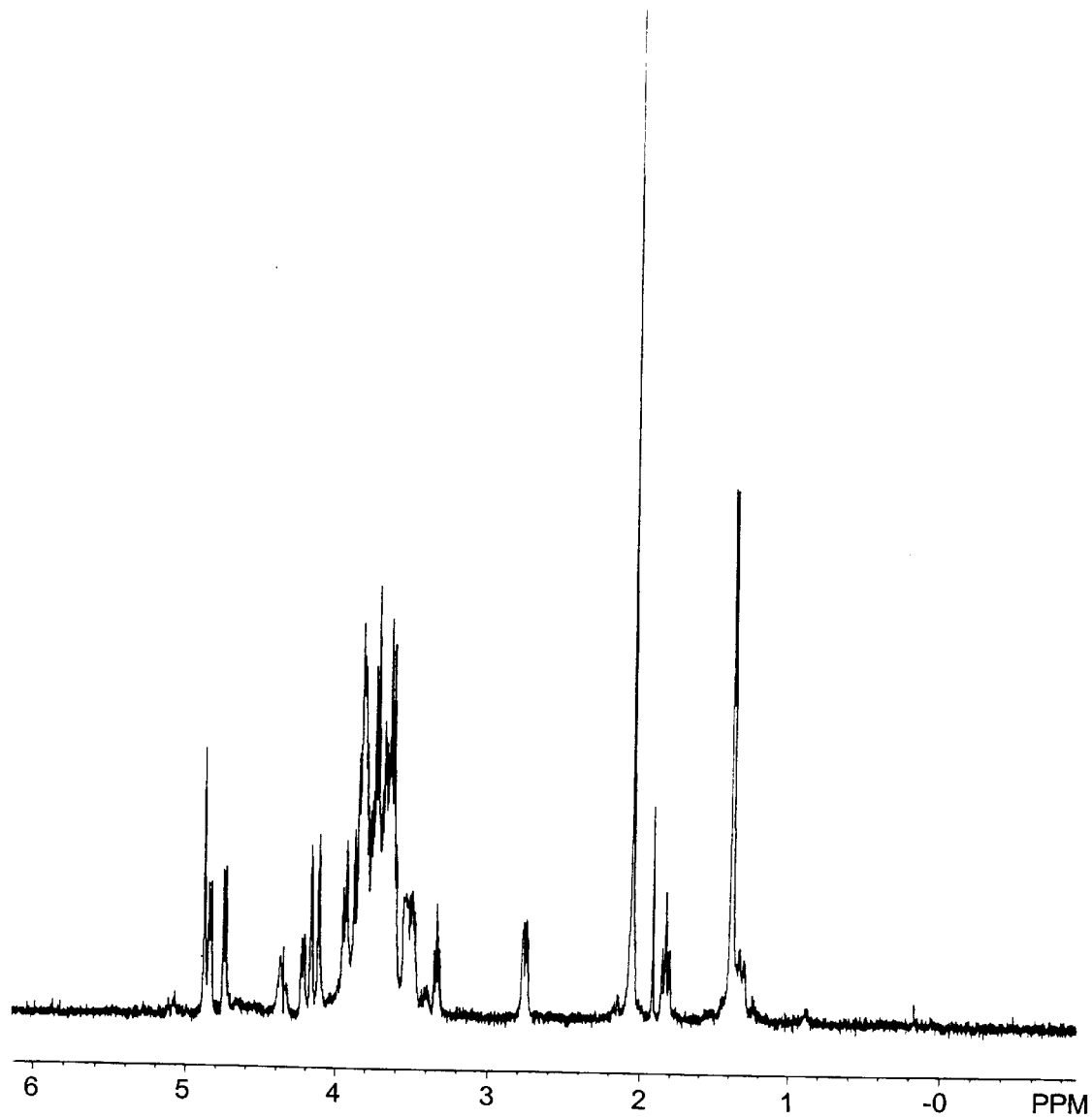
FIG. 5 is the $^1$H NMR spectrum of pooled 7 Kda saccharide fragments generated from type VIII GBS polysaccharide after treatment with ozone.

The $^1$H NMR spectrum of pooled fragments with average molecular weights of 7 kDa is shown in FIG. 5. There are three anomeric proton resonances between 4.8 and 5.0 ppm from the glucose, galactose, and rhamnose residues, respectively. The doublet at 1.4 ppm is due to the 6-deoxy protons of the rhamnose residue. The signals at 2.9 ppm and 1.9 ppm are due to the 3-H of the sialic acid residue. The spectrum of the pooled 7-kDa fractions is identical to that of the native polysaccharide, indicating that the saccharide retained the parental repeat structure.

Figure 6:
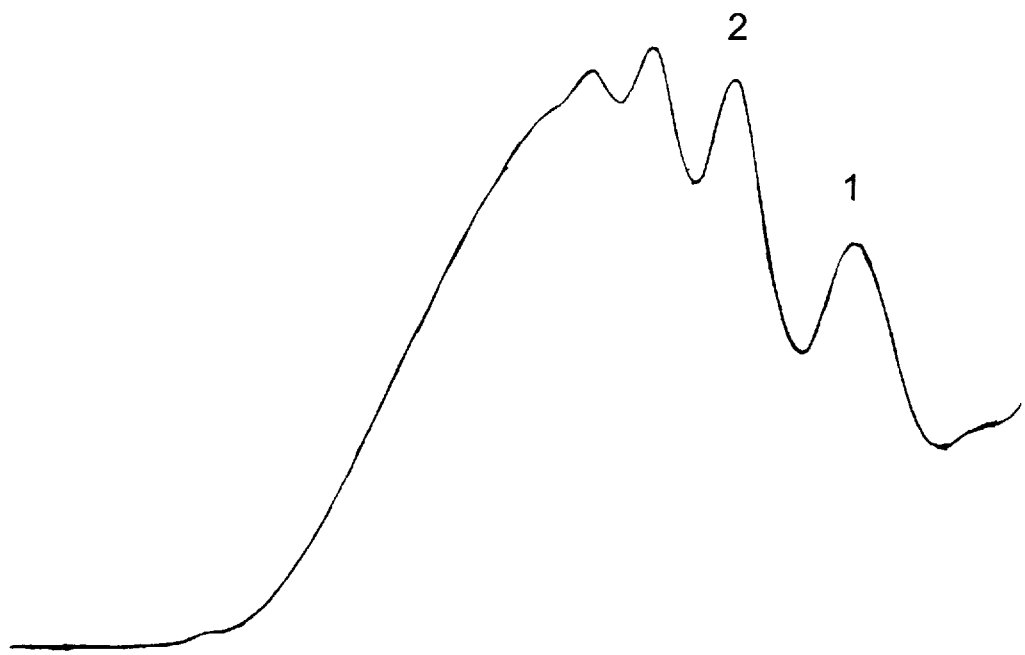
FIG. 6 is a graph showing the elution profile of saccharide fragments generated from type III GBS capsular polysaccharide after treatment with ozone.

Example 3
Generation of Saccharide Fragments from Type III GBS Polysaccharides Using the Three-step Ozonolysis Procedure The LC profile of saccharide fragments generated upon treatment of type III GBS polysaccharides with ozone is shown in FIG. 6. Saccharide fragments were separated on a Superdex 75 column and eluted with 0.3 m M PBS. Peaks 1 and 2 correspond to saccharide fragments containing two and three copies of the type III repeats, respectively.

Figure 7A:
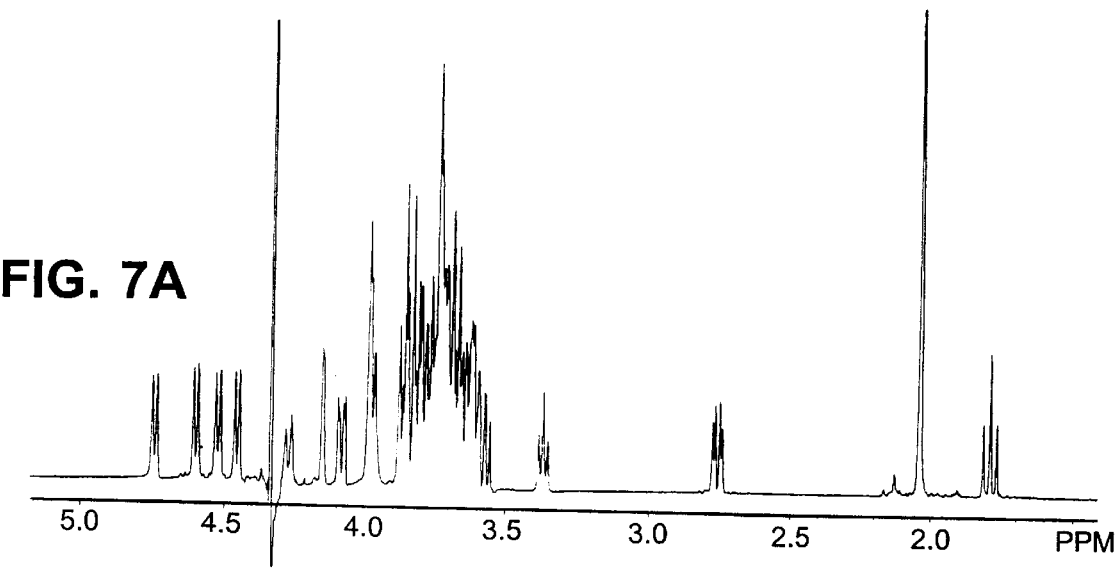
FIGS. 7A–7C are the $^1$H NMR spectra of type III GBS native polysaccharides (A), and ozonolysis-generated saccharide fragments of three (B) and two (C) repeating units.
Figure 7B:
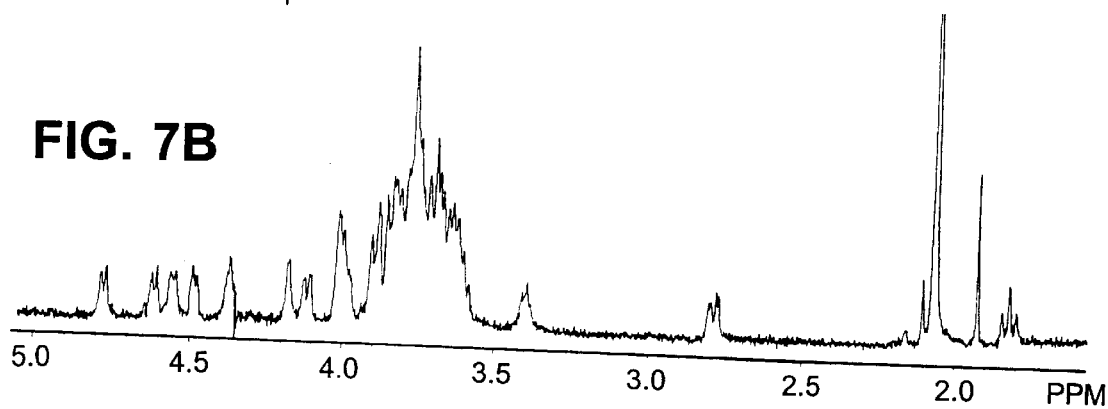
Figure 7C:
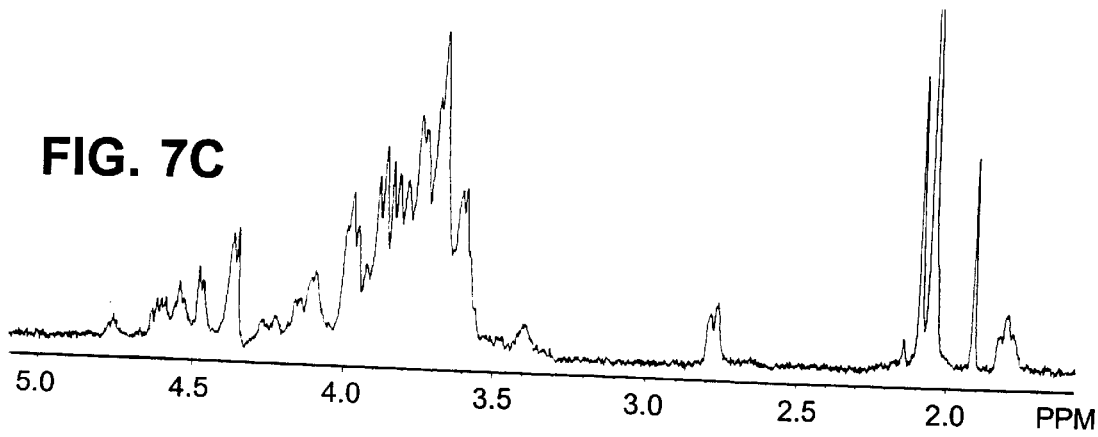
Figure 8A:
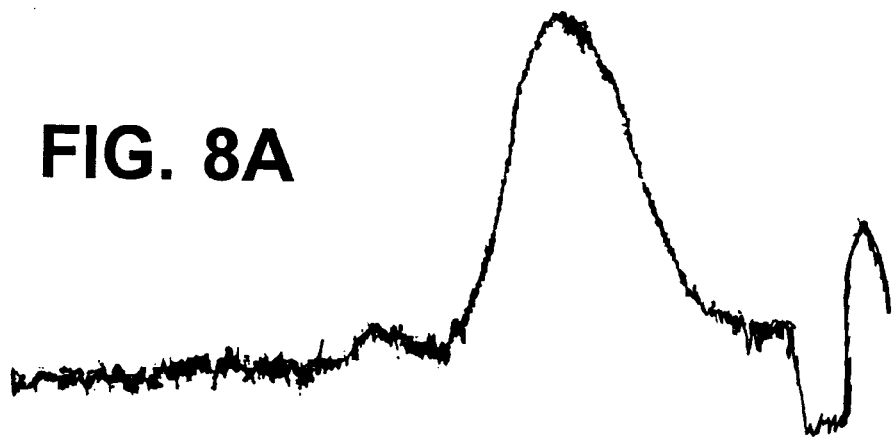
FIGS. 8A–8D are graphs showing the elution profiles of the saccharide fragments generated from type III GBS polysaccharide following treatment with ozone for 150, 195, 270, and 355 minutes, respectively.
Figure 8B:
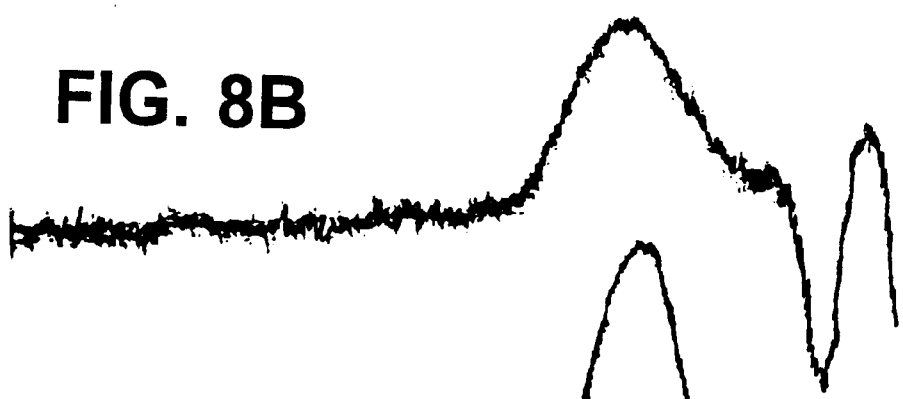
Figure 8C:
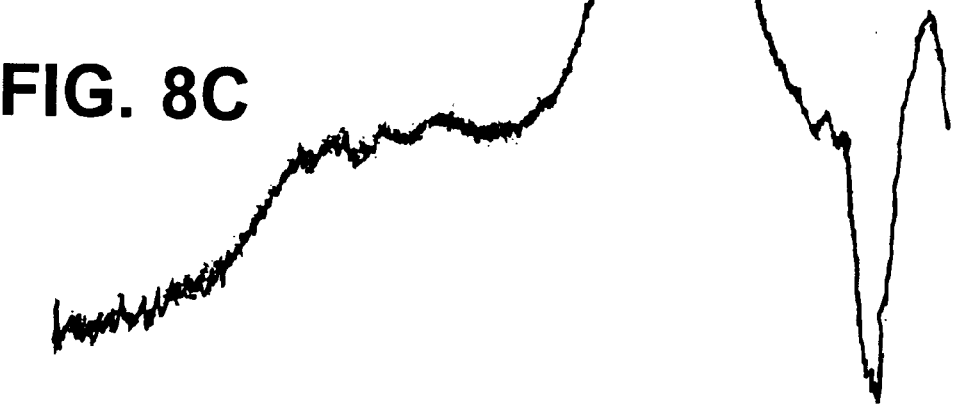
Figure 8D:
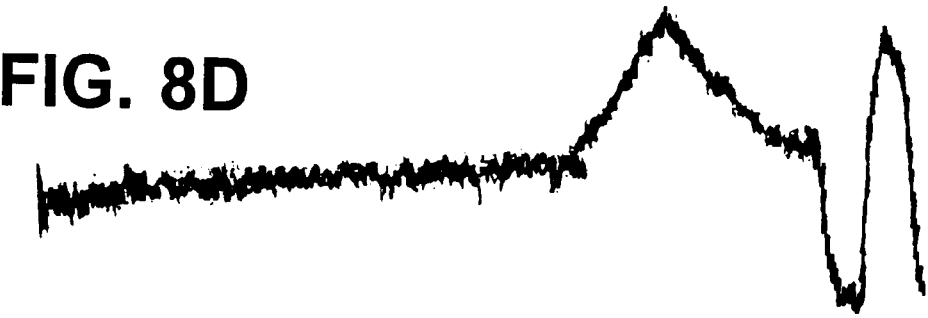

FIGS. 7A–C shows the $^1$H NMR spectra of the native type III GBS polysaccharide and of peaks 2 and 1 of FIG. 6, respectively. The native polysaccharide (FIG. 7A) has a pentasaccharide repeating unit, as revealed by the four anomeric protons (between 4.4 ppm and 4.8 ppm) from the four hexose residues, and a sialic acid residue, as revealed by its 3-H resonance at 2.77 ppm and 1.80 ppm. Peak 2 (FIG. 7B) is mainly a saccharide of three repeating units. Its NMR spectrum is identical to that of the native polysaccharide. Peak 1 (FIG. 7C) corresponds to a saccharide of two repeating units (10 residues). There are seven hexose residues as shown by the 7 anomeric signals at 4.78 ppm (1), 4.63 ppm (2), 4.55 ppm (2), and 4.48 ppm (2). In addition, there are two sialic acid residues and a terminal aldonic acid residue. The sialic acid residue is retained in all fragments, as indicated by its 3-H signals at 2.77 ppm and 1.80 ppm in all the spectra.

The effect of ozonolysis lasting for various periods on type III polysaccharides was examined. FIGS. 8A–8D shows the LC profile after ozonolysis for 150, 195, 270, and 355 minutes, respectively. At each time point, the saccharides generated were of uniform size and fell within narrow size distributions.

The sizes of the saccharide fragment products for each duration of ozonolysis were determined with a Superose 12 column, which has a size separation range of 1–300 kDa. The average sizes of the saccharides at the time points shown in FIGS. 8A through 8D corresponded to 42, 23, 21, and 20 kDa, respectively. Upon prolonged reaction times of 455, 625, and 820 minutes, the average sizes of the saccharides obtained were 16, 14, and 5 kDa, respectively (data not shown).

Figures 9A, 9B:
FIGS. 9A–9B are graphs showing the repeating unit structure of polysaccharide A of *Bacteroides fragilis* (9A), and the elution profile following liquid chromatography of the saccharide fragments generated from polysaccharide A of *Bacteroides fragilis* (9B).

Example 4
Generation of Saccharide Fragments from Polysaccharide A of Bacteroides fragilis Using the Three-step Ozonolysis Procedure The repeating unit of the polysaccharide A from Bacteroides fragilis has the structure shown in FIG. 9A. FIG. 9B shows the LC profile of the saccharides generated upon ozonolysis treatment of the Bacteroides fragilis polysaccharide A using a Superdex75 column. The average molecular weights for peaks 1–3 were 2.1, 4.3, and 6.6 kDa, respectively.

Example 5
Preparation of Tetanus Toxoid Conjugate Vaccine Using Saccharide Fragments Produced by the Three-step Ozonolysis Procedure A saccharide fragment from a type III GBS polysaccharide (5 mg) obtained after ozonolysis was dissolved in 0.375 ml of water and oxidized with 0.125 ml of 0.01 M sodium metaperiodate at room temperature in the dark for 90 minutes (Wessels et al., J. Clin. Invest. 86:1428 (1990)). The mixture was then dialyzed against water and lyophilized. The oxidized saccharide sample was combined with 4 mg of tetanus toxoid, and the combination was dissolved in 0.3 ml of 0.1 M NaHCO$_3$ (pH 8.2), with 20 mg of sodium cyanoborohydride added. The mixture was incubated at 37° C. overnight. The conjugate vaccine product was purified on a S-300 column (Pharmacia).

Example 6
Generation of Saccharide Fragments from -Containing Polysaccharides and -Containing Polysaccharides Using the One-step Ozonolysis Procedure To determine if ozonolysis could be performed using the one-step procedure, polysaccharides of GBS type III, type 14 S. pneumoniae, or dextran were used as the starting material.

A sample of GBS type III polysaccharide (8.3 mg) was dissolved in 1 ml of water and bubbled with ozone for 47 minutes. During this time the pH of the solution was monitored. The reaction mixture became slightly acidic after 20 minutes of ozonolysis, at which time a few drops of a 0.033 M NaHCO$_3$ solution was added until the solution returned to neutral pH. At various time intervals, a 30 1 aliquot of the reaction mixture was taken and screened on a Superose 12 column to check the size of the products.

Figure 10:
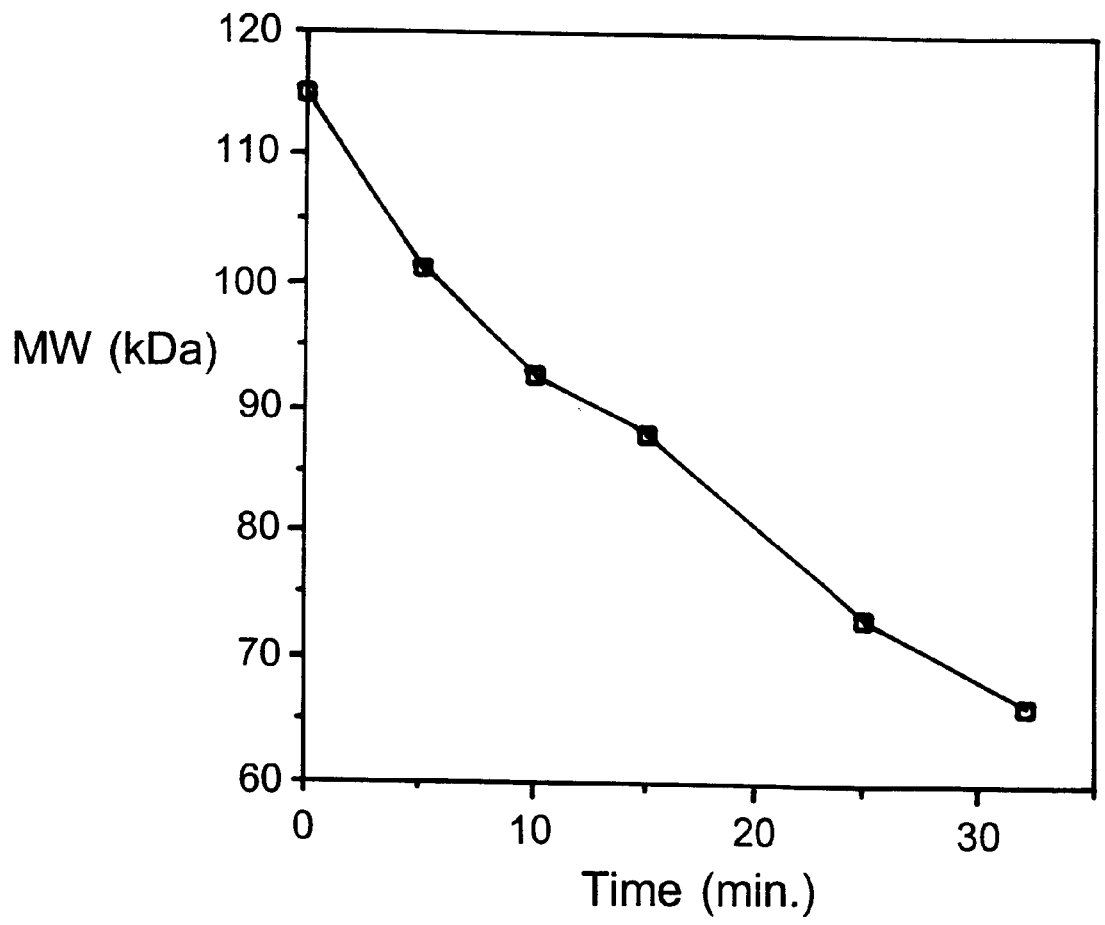
FIG. 10 is a graph showing the molecular weight of saccharide fragments after treatment of a starting type III GBS polysaccharide with ozone for the indicated lengths of time.

As is shown in FIG. 10, the size of the products decreased vary rapidly. After 32 minutes, the reaction again became acidic, and 0.1N NaOH was added until the pH of the solution reached 9. The reaction was continued for another 15 minutes, during which time the pH of the solution remained unchanged. The average molecular weight of the final saccharide fragment was 4.4 kDa. The product was purified on a P2 Biogel column (Biorad, Hercules, Calif.) and eluted with water on a FPLC system. One major peak was obtained.

Figure 11:
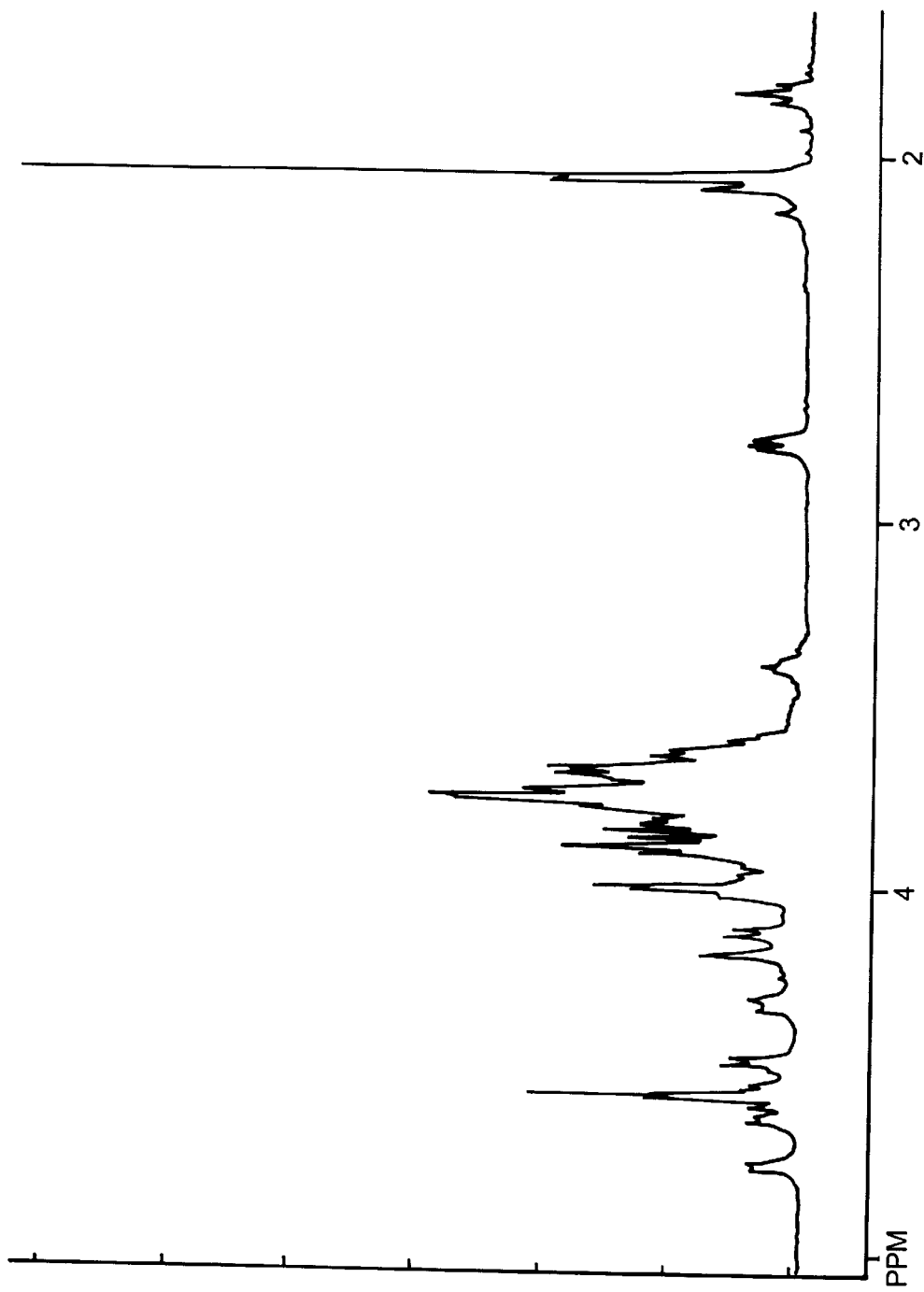
FIG. 11 is the $^1$H NMR spectrum of type III GBS native polysaccharides following ozonolysis in NaHCO$_3$ buffer.

The collected fractions from the FPLC column were then pooled, lyophilized, and subjected to $^1$H NMR spectroscopy. The $^1$H NMR spectrum is shown in FIG. 11. The spectra was identical to that of the starting polysaccharide, thus demonstrating that the saccharide fragment product has the same subunit structure as the starting polysaccharide. In particular, the acid-labile sialic residue of the type III GBS was retained as shown by the characteristic H-3 resonances at 2.8 and 1.8 ppm. These data suggest that ozonolysis using the one-step procedure results in saccharide fragments having the same internal repeat structure as the starting polysaccharide. The one-step ozonolysis method was also carried out using the type 14 S. pneumoniae polysaccharide as the starting substrate. A 10.5 mg sample was dissolved in 5 ml of 0.033 M NaHCO$_3$ solution and ozonized for 5 hours. During the ozonolysis 75 1 aliquots of the reaction mixture were taken and screened on a Superose 12 sizing column. The native polysaccharide has an average molecular weight of 130 kDa. After the reaction had proceeded for 30, 140, and 330 minutes, the size of the saccharides in the reaction mixture decreased to 23, 6, and 3 kDa, respectively. $^1$H NMR analyses of the saccharide fragments revealed that the internal structure of the polysaccharide was conserved in these fragments. The results using type III GBS polysaccharide and type 14 *S. pneumoniae* polysaccharide demonstrate that polysaccharides containing linkages can be cleaved to saccharide fragments while retaining the subunit linkages. To determine if saccharide fragments could also be produced from a polysaccharide containing linkages, the one-step ozonolysis procedure was carried out using dextran as the starting polysaccharide. Dextran is a polysaccharide composed exclusively of the D-glucopyranosyl units connected via an -(1,6) linkage.

A 4.9 mg sample of dextran (molecular weight of 110 kDa) was dissolved in 2.4 ml of 0.03 M $NaHCO_3$ and subjected to ozonolysis for 2.5 hours, with periodic monitoring of the pH of the solution. The solution gradually became acidic, and at the termination of the ozonolysis reached a pH of 1. The size of the reaction products was monitored and found to be 300 Da. These results demonstrate that polysaccharides containing-linkages can also be cleaved using ozonolysis.

In addition to the above-described application of the one-step ozonolysis procedure to polysaccharides derived from GBS type III and *S. pneumoniae* type 14, this method has also been used successfully to produce saccharide fragments from *B. fragilis* type A, cellobiose, and lactose.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for producing antibodies specific for a saccharide fragment, said method comprising:
    a) providing an immunogen comprising a saccharide fragment product conjugated to a carrier, said saccharide fragment product being produced by degrading a larger polysaccharide, the polysaccharide being larger than the saccharide fragment product and said polysaccharide comprising at least one covalent bond between a C1 anomeric carbon of an aldose residue and an oxygen atom of a second residue in a -D or -L glycosidic linkage; said degrading comprising:
        1) protecting free hydroxyl groups on the larger polysaccharide;
        2) reacting the larger polysaccharide with ozone to oxidize the C1 anomeric carbon, thus converting the aldose residue to an aldonic acid ester residue; and
        3) cleaving the aldonic acid ester residue to form the saccharide fragment; and
    b) administering said immunogen to a suitable host.

2. The method of claim 1 wherein said polysaccharide contains sialic acid.

3. The method of claim 1 wherein said polysaccharide is a group B Streptococcus capsular polysaccharide.

4. The method of claim 1 wherein said polysaccharide is the O-antigen of a lipopolysaccharide.

5. The method of claim 1 wherein said polysaccharide is a capsular polysaccharide of *Staphylococcus aureus*.

6. The method of claim 5 wherein said polysaccharide is the capsular polysaccharide of *Staphylococcus aureus* type 5 or *Staphylococcus aureus* type 8.

7. The method of claim 1 wherein said polysaccharide is the capsular polysaccharide of *Streptococcus pneumonia*.

8. The method of claim 1 wherein said polysaccharide is the capsular polysaccharide of *Bacteroides fragilis*.

9. The method of claim 1 wherein said polysaccharide is selected from the group consisting of GBS type II polysaccharide, GBS type III polysaccharide, *Bacteroides fragilis* capsular polysaccharide, and GBS type VIII polysaccharide.

10. The method of claim 1 wherein the ozone is added as a solution.

11. The method of claim 1 wherein the ozone is generated in-situ.

12. The method of claim 1 wherein the ozone is delivered from an external source.

13. The method of claim 1 wherein the ester is cleaved by a nucleophile.

14. The method of claim 13 wherein the nucleophile is a hydroxyl ion.

15. The method of claim 13 wherein the nucleophile is an amine.

16. The method of claim 14 wherein the nucleophile is a thiol.

17. The method of claim 14 wherein the nucleophile is a carbanion.

18. The method of claim 1 wherein the ester is cleaved by heating.

19. The method of claim 1 wherein the hydroxyl groups are protected by forming ester groups.

20. A method for producing antibodies specific for a saccharide fragment, said method comprising:
    a) providing an immunogen comprising a saccharide fragment product conjugated to a carrier, said saccharide fragment product being produced by oxidizing a larger polysaccharide, the polysaccharide being larger than the saccharide fragment and comprising at least one covalent bond between a C1 anomeric carbon of an aldose residue and an oxygen atom of a second residue in a glycosidic linkage; the oxidizing comprising reacting the larger polysaccharide in an aqueous solution with ozone to yield a mixture comprising the saccharide fragment product; and
    b) administering said immunogen to a suitable host.

21. The method of claim 20 wherein said covalent bond between the C1 anomeric carbon of the aldose residue and the oxygen atom of the second residue is in an glycosidic linkage.

22. The method of claim 20 wherein said covalent bond between the C1 anomeric carbon of the aldose residue and the oxygen atom of the second residue is in a glycosidic linkage.

23. The method of claim 22 wherein said larger polysaccharide reacts with ozone to oxidize the C1 anomeric carbon, thus converting the aldose residue to an aldonic acid ester residue.

24. The method of claim 22 wherein said polysaccharide is a group B Streptococcus capsular polysaccharide.

25. The method of claim 22 wherein said polysaccharide is the O-antigen of a lipopolysaccharide.

26. The method of claim 22 wherein said polysaccharide is a capsular polysaccharide of *Staphylococcus aureus*.

27. The method of claim 26 wherein said polysaccharide is the capsular polysaccharide of *Staphylococcus aureus* type 5 or *Staphylococcus aureus* type 8.

28. The method of claim 20 wherein said polysaccharide is the capsular polysaccharide of *Streptococcus pneumonia*.

29. The method of claim 20 wherein said polysaccharide is the capsular polysaccharide of *Bacteroides fragilis*.

30. The method of claim 20 wherein said polysaccharide is selected from the group consisting of GBS type II polysaccharide, GBS type III polysaccharide, *Bacteroides fragilis* capsular polysaccharide, and GBS type VIII polysaccharide.

31. The method of claim 20 wherein the ozone is added as a solution.

32. The method of claim 20 wherein the ozone is generated in-situ.

33. The method of claim 20 wherein the ozone is delivered from an external source.

34. The method of claim 22 wherein the ester is cleaved by a nucleophile.

35. The method of claim 34 wherein the nucleophile is a hydroxyl ion.

36. The method of claim 34 wherein the nucleophile is an amine.

37. The method of claim 34 wherein the nucleophile is a thiol.

38. The method of claim 34 wherein the nucleophile is a carbanion.

39. The method of claim 23 wherein the ester is cleaved by heating.

* * * * *